United States Patent [19]

Longo

[11] 4,129,456
[45] Dec. 12, 1978

[54] METHOD OF REMOVING DENTAL CEMENT

[75] Inventor: James J. Longo, Wilmington, Del.

[73] Assignee: DHP Corporation, Wilmington, Del.

[21] Appl. No.: 766,701

[22] Filed: Feb. 8, 1977

[51] Int. Cl.$^2$ .................... B08B 3/08; B08B 3/12
[52] U.S. Cl. ........................................ 134/1; 32/1;
134/3; 134/38; 134/41; 134/42; 252/DIG. 5
[58] Field of Search ............ 134/1, 3, 38, 42, 41;
252/DIG. 5, DIG. 8, 142, 143; 106/35; 32/1

[56] References Cited

U.S. PATENT DOCUMENTS

| 2,142,780 | 1/1939 | Fortney | 32/1 |
|---|---|---|---|
| 2,303,932 | 12/1942 | Guild | 252/DIG. 5 |
| 3,574,123 | 4/1971 | Laugle | 134/38 X |
| 3,997,459 | 12/1976 | Bogie et al. | 134/3 X |
| 3,998,654 | 12/1976 | Falaas et al. | 134/38 X |
| 4,024,085 | 5/1977 | Kobayashi et al. | 134/38 X |
| 4,032,627 | 6/1977 | Suchan et al. | 106/35 X |

OTHER PUBLICATIONS

Cruse et al., "Waterless Hand Cleaners," *Soap and Chem. Specialties*, Nov. 1963, pp. 41–42, 103–104.

*Primary Examiner*—Marc L. Caroff
*Attorney, Agent, or Firm*—Connolly and Hutz

[57] ABSTRACT

Carboxylate cement is removed from dental products by use of a solution containing an organic acid having a COOH radical. A preferred organic acid is citric acid.

6 Claims, No Drawings

METHOD OF REMOVING DENTAL CEMENT

BACKGROUND OF THE INVENTION

Carboxylate cements are conventionally used in the dental art for various purposes such as securing temporary or permanent bridges. In the application of these dental appliances various dental tools such as spatulas have the dental cement adhered thereto and these tools must later be cleaned. It is customary to attempt cleaning the dental cement from such tools by a utilization of a 10–20% solution of sodium hydroxide. This conventional practice, however, has a number of drawbacks. For example, such a solution of sodium hydroxide is corrosive, harmful to the eyes and discolors the hands. Additionally, the cleaning action is not completely effective, while also being time consuming. Such cleaning solutions are also caustic, corrosive and a primary skin irritant and thus fall under FDA cautionary requirements.

SUMMARY OF THE INVENTION

An object of this invention is to provide an efficient, reliable and economic method for removing carboxylate cements from dental products or the skin of the user such as hands, gingiva, etc.

A further object of this invention is to provide such a method wherein the solvent does not have the harmful affects of conventional dental solvents.

A still further object of this invention is to provide such a method which can be used for various dental appliances without the numerous drawbacks of conventional cleaners such as NaOH.

In accordance with this invention a solution of an organic acid having a COOH radical dissolved in a carrier liquid is applied to the dental product to loosen the adherence of the carboxylate cement thereto for cleaning the dental product. A preferred organic acid is citric acid which is particularly advantageous because of its ready availability and thus low cost and because citric acid acts as a brightening agent for particular dental products such as those made from stainless steel. In a preferred practice of the invention the dental product is immersed in the solvent in an ultrasonic cleaner to thereby utilize the mechanical agitation from the ultrasonic cleaner to enhance the removal of the carboxylate cement.

DETAILED DESCRIPTION

Carboxylate cements are utilized for various dental purposes. One such cement is commercially marketed under the name "Durelon" and is described in U.S. Pat. No. 3,655,605 as being a polyacrylic acid containing dental cement. The hardened dental cement is prepared by mixing a surgical grade metal oxide powder with an aqueous solution containing from about 20% to about 60% of polyacrylic acid having a viscosity determined average molecular weight of from about 5,000 to about 250,000. Although carboxylate cements are of relatively recent origin, the cements have many uses. For example, temporary and permanent bridges are mounted in place with such cements. This is accomplished by applying the cement through use of a spatula to the bridge, to the abutting teeth and on the gingiva. The bridge is then mounted in place and excess cement is removed. Within a few minutes the cement is cured. Some cement, however, remains on such tools as the spatula, explorers, etc. These dental instruments must be cleaned for further use.

In accordance with the invention a solvent for removing the carboxylate cement is prepared by utilizing an organic acid having the COOH radical, which has been found to be highly effective in attacking such carboxylates by the organic acid acting on the alkaline. Various types of organic acids may be used within the broad concepts of this invention. Such organic acids include, for example, glutonic, tartaric, malic, formic, lactic and acetic. Other suitable acids are benzoic, salicylic, alicylic and amino acids which contain both $NH_2$ and COOH. These organic acids, however, have various drawbacks such as relative unavailability or expense or have characteristics rendering them unsuitable for dental use. Of all the organic acids, however, citric acid has been found to best fulfill the purposes of this invention. In this respect citric acid is readily available and does not have the cautions which would render it undesirable for dental use. Moreover, citric acid is particularly advantageous since it is a metal brightener and thus not only removes the carboxylate cement from various dental products, particularly stainless steel products, but actually improves the appearance of the products. Such citric acid also acts as a brightener for such materials as gold, platinum, chrome-cobalt alloys, porcelain, acrylic, the non-precious alloys presently available, and silver solders used in orthodontic appliances, as well as stainless steel. Such materials are hereinafter referred to as brightenable materials.

In a preferred practice of this invention 200 grams of citric acid is added to 500 ml of warm tap water and the solution is placed in an ultrasonic cleaner. The citric acid may be anhydrous or monohydrate. Although anhydrous has the disadvantage of being more expensive, both forms work equally well as long as the 200 grams monohydrate citric acid equals the 200 grams of anhydrous citric acid. The dental product is then immersed in the cleaner and the carboxylate cement is quickly removed by the combination of actions from the citric acid and from the ultrasonic cleaner. A conventional citric acid is used. The anhydrous citric acid has a chemical formula of $C_6H_8O_7$, while the monohydrate has a chemical formula of $C_6H_8O_7 \cdot H_2O$.

The citric acid is further advantageous since it is compatible with various additives. Thus, for example, the solution may include flavoring substances such as orange or lime flavorings, or might include perfumants or coloring substances which would render it more appealing to the user. Also a variety of surfactants may be employed as surface tension breakers and penetrants, anionic, cationic, nonionic.

By way of contrast, for example, an effective cleaning operation utilizing the above concentrated solution takes place in only three minutes, as contrasted to periods of time exceeding one hour with a conventional 20% solution of sodium hydroxide for cleaning an equivalent amount of carboxylate cement. Thus the citric acid is quicker, more economical and avoids the cautions attendant with sodium hydroxide cleaning solutions.

While a concentration of 200 grams citric acid to 500 ml of water is preferred, the concentration may be lower with the realization, however, that lower concentrations are relatively less effective. A concentration of at least 50 grams per 500 ml (i.e. a ratio of 1:10) is workable but not as desired as the preferred ratio of 1:2.5 (i.e. 200 grams per 500 ml) with 1:1.125 being the preferred upper ratio. The solution may include liquids other than water. Alcohol, for example, works quite well but is more expensive and is flammable. Similarly, glycerol or propylene glycol may be used in place of water. Further various forms of suitable acids may be mixed in forming the solution.

The concepts of this invention may be practiced in conjunction with various dental techniques. For example, when an abutment tooth juxtaposed a bridge must be removed it may be necessary to also remove the bridge. Frequently, a pontic or spacer is made out of the abutment and it is first necessary to remove the cement. The present practice is to utilize a drill for cement removal purposes. A drawback with this practice, however, is that the drill might penetrate the crown or the drilling may affect the type of fit for the bridge since it could result in the bridge rocking which might loosen the adjacent tooth and abutment teeth. By utilizing the inventive method wherein a citric acid solution is applied in situ the drilling step can be eliminated since the cement would be removed by the citric acid solution alone.

The invention may also be practiced in removing cement from pontics which must be replaced. Such pontics sometimes have a "Steeles" facing. The back of the tooth has a slot in the facing which is filled with cement. If the facing splits, the cement must be removed to permit replacement. Frequently, such cement removal operation is particularly difficult because of the relatively inaccessible location of the cement. The invention thus has particular utility in such situations by permitting the easy application of the solvent in these relatively inaccessible locations.

Citric acid, having a very low toxicity and none of the numerous drawbacks of the strong acids, may thus be used directly in the mouth when removing and replacing a "Steeles" facing or pontic. For such direct human application it is preferable to adjust the pH to approximately 6. A similar use is to apply the citric acid to the gingiva to remove excess cement resulting from mounting a crown or the like. Such application may be conveniently effected by means of a cotton swab or similar applicator.

The invention may also be practiced to remove such cement from the technician's hands by simply washing the hands in the solution. Again with such human application a strong acid or base should be avoided the preferred pH is about 6.

Fatty acids such as oleic and stearic acids also have a very definite advantage since both are organic and weak acids and contain the COOH radical as a scrub for the technician's hands in the removal of carboxylate cements.

As is apparent the invention may be practiced in a number of different ways. In these various practices the pH would be adjusted, as necessary. For example, the pH may be as low as 1.02 or as high as 6.9. A pH value of 3-5 is preferred with the value of 3-3.2 being effective for cleaning dental products while a value of about 6 is preferable for direct human application.

For cleaning dental products the invention is generally practiced by placing the article in a glass beaker containing a full strength solvent of this invention. An ultrasonic cleaning unit may optionally be used where a more rapid action is desired. The articles, which may conveniently be soaked overnight, are rinsed with tap water after processing. For removal of carboxylate cement from the skin, the solvent is applied directly to the affected areas. The skin is then massaged until the cement is removed and the skin is rinsed.

The solvent of this invention, particularly where citric acid is employed, is thus highly effective for removal of carboxylate cement from crowns, bridges, facings, instruments, etc., while also being ideally suited for removal of cement from the skin. The practice of the invention eliminates drilling and manual cleaning, eliminates the need and use of strong acids or alkalines and is safe, mild, non-corrosive and preferably water-based.

What is claimed is:

1. In a method of removing from a surface a hardened dental cement prepared by mixing a surgical grade metal oxide powder with an aqueous solution containing from about 20% to about 60% of polyacrylic acid having a viscosity determined average molecular weight of from about 5,000 to about 250,000 the improvement comprising forming a substantially aqueous or alcoholic solution of citric acid having a concentration of at least 1 gram citric acid per 10 ml of solution, and applying an amount of said solution to the surface effective to remove said cement.

2. In the method of claim 1 wherein the surface is on a dental product, placing the solution in an ultrasonic cleaner, and immersing the cement containing dental product in the citric acid solution, and utilizing mechanical agitation from the ultrasonic cleaner to enhance the removal of the cement.

3. In the method of claim 1 wherein the citric acid solution has a concentration no more than about 1 gram citric acid per 1.125 ml of water.

4. In the method of claim 1 wherein the surface is the skin of a human, and applying the citric acid solution by massaging the skin with said solution.

5. In the method of claim 4 wherein the skin is the gingiva, and applying the solution by an applicator.

6. In the method of claim 4 wherein the skin is on the hands, and applying the solution by washing the hands therein.

* * * * *